United States Patent [19]
Lefebvre

[11] Patent Number: 5,376,100
[45] Date of Patent: Dec. 27, 1994

[54] ROTARY ATHERECTOMY OR THROMBECTOMY DEVICE WITH CENTRIFUGAL TRANSVERSAL EXPANSION

[76] Inventor: Jean-Marie Lefebvre, 219, boulevard de la liberté 59800 Lille, France

[21] Appl. No.: 239,940

[22] Filed: May 5, 1994

Related U.S. Application Data

[63] Continuation of Ser. No. 992,427, Dec. 17, 1992, abandoned.

[30] Foreign Application Priority Data

Dec. 23, 1991 [FR] France .................. 91 16422

[51] Int. Cl.⁵ .............................. A61B 17/32
[52] U.S. Cl. ........................ 606/180; 604/22
[58] Field of Search ............... 128/751, 755; 604/22, 29, 52, 53; 606/167, 168, 170, 171, 180, 194

[56] References Cited

U.S. PATENT DOCUMENTS

| | | | |
|---|---|---|---|
| 4,790,813 | 12/1988 | Kensey | 604/22 |
| 4,886,061 | 12/1989 | Fischell et al. | 604/22 |
| 5,030,201 | 7/1991 | Palestront | 128/755 |
| 5,100,424 | 3/1992 | Jong et al. | 606/159 |
| 5,192,291 | 3/1993 | Pannek, Jr. | 604/22 |

FOREIGN PATENT DOCUMENTS

| | | |
|---|---|---|
| 0315290 | 5/1989 | European Pat. Off. |
| 0379784 | 8/1990 | European Pat. Off. |
| 0419154 | 3/1991 | European Pat. Off. |
| 0426322 | 5/1991 | European Pat. Off. |

Primary Examiner—C. Fred Rosenbaum
Assistant Examiner—N. Kent Gring
Attorney, Agent, or Firm—Ladas & Parry

[57] ABSTRACT

The atherectomy or thrombectomy device according to the invention comprises a rotary member composed of flexible filiform elements, which are joined by their two ends, the distal end and the proximal end; it contains no mechanical means for bringing said ends closer and the speed of rotation of the rotary member is sufficient, notably higher than 30,000 rays/min. to achieve the transversal expansion of the filiform elements under the effect of the centrifugal force.

Preferably, the rotary member is constituted by a conduit, such as a conduit in polytetrafluoroethylene provided with one or two sets of longitudinal slits symmetricaly distributed over its periphery and defining flexible strips.

8 Claims, 1 Drawing Sheet

ROTARY ATHERECTOMY OR THROMBECTOMY DEVICE WITH CENTRIFUGAL TRANSVERSAL EXPANSION

This is a continuation of copending application(s) Ser. No. 07/992,427 filed on Dec. 17, 1992, now abandoned.

FIELD OF THE INVENTION

The present invention relates to an atherectomy or thrombectomy device, namely a device intended for destroying hard deposits which have formed on the wall of a blood vessel, such as for example the atheroma plaque inside the coronary artery (atherectomy), or for fragmenting the thrombi obstructing the lumen of a blood vessel (thrombectomy). For simplification purposes, the term atherectomy will be mentioned throughout this text, knowing that atherectomy or thrombectomy are concerned, as well as the term deposits, knowing that it may also designate thrombi.

The present invention relates more particularly to a rotary atherectomy device which comprises a rotary member capable of eroding or attacking the material constituting the deposits or occlusions on the walls of the vessels.

BACKGROUND OF THE INVENTION

The currently well known technique of angioplasty presents many limitations. This technique consists in introducing an inflatable bag as far as the shrunk area of the vessel where the deposits are situated and in inflating said bag by means of fluid until pressures of about 5 atmospheres are reached. The primary object of this technique is not to remove deposits but to clear the vessels. The deformation due to the force applied by the inflated bag on the deposits can, in a large number of cases, be reversible and cause more stenoses in patients who have been treated by angioplasty.

Attempts have been made during the last few years, to remove deposits by a destructive action, more particularly with a rotary tool adapted to remove, superficially, the material constituting the deposit.

In document EP 0086048, the rotary tool comprises a body of ellipsoid shape along which extends at least one helical-shaped edge. This tool is a high speed cutting and abrasive tool which, by turning, is capable of cracking and removing the relatively hard intra-arterial deposits, without damaging the arterial walls, by repeatedly hitting said deposits with one or more of the cutting faces provided on the edge or edges.

In the device described in document EP 0086048, the rotary tool has an attacking diameter which is constant and therefore gives no possibility for adapting the destroying action as a function of the extent of the deposits, hence of the obstruction of the vessel.

A rotary atherectomy device has already been proposed in document EP 0442137, in which the rotary tool can have an adjustable configuration. Said rotary tool is composed of flexible filiform elements which are joined together by their distal and proximal ends; this device further comprises a system for bringing the two ends axially closer, such as for example a pull-in wire actuatable by the operator which makes it possible to bring the distal end of the rotary tool towards the proximal end of the flexible filiform elements. During this closing-in movement, each filiform element bends, this leading to a transversal expansion of the rotary tool.

Given that the filiform elements are, during their introduction, approximately rectilinear, the rotary tool can be introduced into the vessel with a catheter of small dimension. This is a great advantage over the tool which has a constant attacking diameter for which the introduction catheter has to have an inner diameter smaller than the diameter of the rotary tool. Nonetheless, the device described in document EP 0442137 is relatively complex in design, particularly because of the presence of the means for bringing axially closer the two proximal and distal ends of the filiform elements constituting the rotary tool. Another device of the same type is described in U.S. Pat. No. 5,030,201.

SUMMARY OF THE INVENTION

It is the object of the invention to provide a rotary atherectomy device which overcomes the aforesaid disadvantage of the prior art devices.

This object is definitely reached by the device according to the invention. This is an atherectomy device which comprises, in known manner, a rotary member composed of flexible filiform elements, joined together by their two ends, a distal end and a proximal end, and transversely expandable by said two ends coming axially closer together.

According to a characteristic of the invention, the device contains no mechanical means for bringing said ends closer; moreover, the flexibility of the filiform elements is sufficient to allow their transversal expansion under the sole effect of the centrifugal force.

It was of course already known from document EP 0 308 957 that it is possible to expand a tool transversely under the effect of the centrifugal force, but what was used in that case was a strip, contained in the body of a rotary member and fast therewith by one of its ends. The transversal expansion of the tool consisted in the axial deviation of the free end of that strip.

It is the merit of the invention to provide a particularly simplified device, in that it is the rotary body itself which expands transversely, and not an added tool as in document EP 0 308 957, and in that there are no added mechanical means for inducing the transversal expansion of the rotary tool, as in documents EP 0 442 137 and U.S. Pat. No. 5,030,201. It is worth noting that a transversal expansion caused by the sole centrifugal force could not have been obtained with the device described in these last two documents, as this would have been prevented by the presence of mechanical means bringing closer together the ends of the flexible filiform elements.

It is therefore the control of the speed of rotation of the tool which enables the operator to act on the attacking diameter of the tool inside the vessel.

It is conceivable that, for a given rotation of the rotary member, the extent of the transversal expansion will be dependent on the length of the filiform elements as well as on their flexibility.

Moreover, according to the Applicant's findings, the transversal expansion of the rotary member, under the sole effect of the centrifugal force, makes it possible for the device according to the invention to better adapt the attacking diameter as a function of the variations in the inner diameter of the vessel.

Preferably, the atherectomy device according to the invention comprises a conduit, capable of being introduced by a catheter into the vessel, which conduit presents towards its front end longitudinal slits distributed symmetrically over its periphery and defining the flexible filiform elements of the rotary member.

According to this preferred version, the flexible filiform elements are thus constituted by the strips formed in the conduit between each slit. It is understood that said slits do not extend as far as the end of the conduit but they stop before that end so that the strips remain joined together by said end. Obviously, this version of the device according to the invention is perfectly simple to produce.

Advantageously, the atherectomy device according to the invention comprises a rigid guide wire, designed to be threaded through the conduit and extending from the front end thereof of a predetermined length.

For the good operation of the device according to the invention, the length of the guide wire which projects from the front end of the conduit, should be sufficient to ensure that said wire rests against the inner wall of the vessel, such that during the rotation of the rotary member, said guide wire does not flap against the wall of the vessel. Understandably, said predetermined length will be dependent on the diameter of the vessel and also on the straightness thereof in the area where the deposit to be eliminated is situated.

The conduit may be produced in polytetrafluoroethylene, which is a material which, on the one hand, is sufficiently flexible to allow the transversal expansion of the precut flexible strips under the sole effect of the centrifugal force, and on the other hand, has a very low friction coefficient so that the sliding of the front end of the conduit along the guide wire during the rotation movement of said conduit causes only a very small loss of energy.

According to a variant embodiment, the flexible filiform elements of the rotary member have an abrasive surface. This version is particularly useful in the case of atherectomy of arteries, in which the deposits have to be comminuted into very fine particles.

In order to obtain this abrasive nature, it is possible either to mix some abrasive powder with the plastic material constituting the conduit, at least in its front part corresponding to the rotary tool, or to glue said abrasive powder on the surface of the flexible filiform elements.

Preferably, according to the device of the invention, the rotary member is composed of two successive sets of flexible filiform elements. This makes it possible to obtain the transversal expansion of a rotary member composed of two tools, placed at a set distance from each other inside the vessel. This possibility was totally excluded when the transversal expansion of the rotary tool was obtained by mechanical means for bringing closer the proximal and distal ends of the flexible filiform elements constituting said tool.

According to the Applicant, this particular arrangement makes it possible to adapt to a maximum the progressive attack of the deposits especially when the length of the filiform elements of the most distal set is less than that of the filiform elements of the most proximal set. What is obtained in such a case, for the same speed of rotation of the rotary member, is, first the action of the first set of filiform elements with a smaller attacking diameter, and then the action of the second set of filiform elements with a greater attacking diameter. This enables clearing and removal of the deposits in the vessels of large diameters, particularly the vena cava.

BRIEF DESCRIPTION OF THE DRAWINGS

The invention will be more readily understood on reading the following description of two examples of embodiment of a rotary atherectomy device with centrifugal transversal expansion, given with reference to the accompanying drawings, in which.

DESCRIPTION OF PREFERRED EMBODIMENTS

Figure 1A:
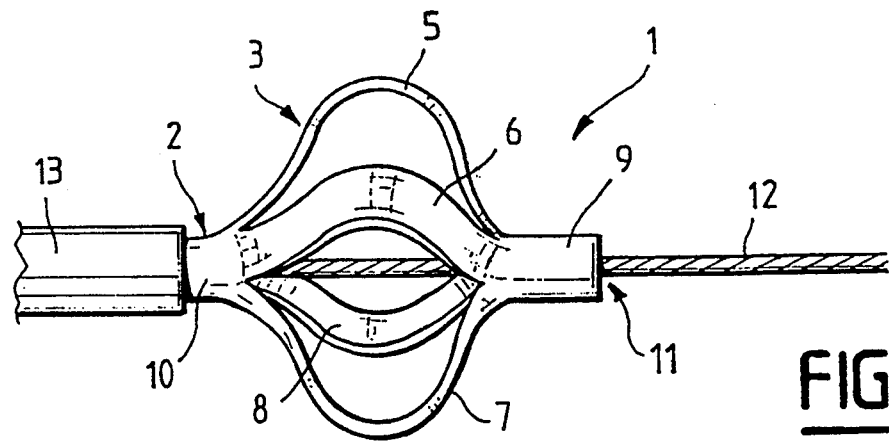
FIGS. 1A and 1B are side views of the device, of its introduction catheter, and of the guide wire, in expanded position (FIG. 1A) and in introduction position (FIG. 1B).

FIG. 1 only shows the front part of the atherectomy device according to the invention. In fact, the illustrated part is only the active part of the device, namely the part which, when rotating, enables the destruction of any abnormal deposits adhering to the inner wall of a blood vessel. Such deposits, as is well known, are a major cause of cardiovascular diseases, when they are intra-arterial atheroma deposits, or atherosclerotic plaques. Such deposits may also affect the function of certain organs.

The atherectomy device I according to the invention comprises a conduit 2 on the front part 3 of which slits 4 are provided, over part of its length and longitudinally, which slits are distributed regularly on its periphery. In the example illustrated in FIG. 1, there are four slits 4 which define four strips 5, 6, 7, 8 of equal width and equal length. The slits 4 do not reach to the front end of the conduit 2, so that the four strips 5–8 remain joined together due to the distal end 9 of the conduit 2.

Figure 1B:
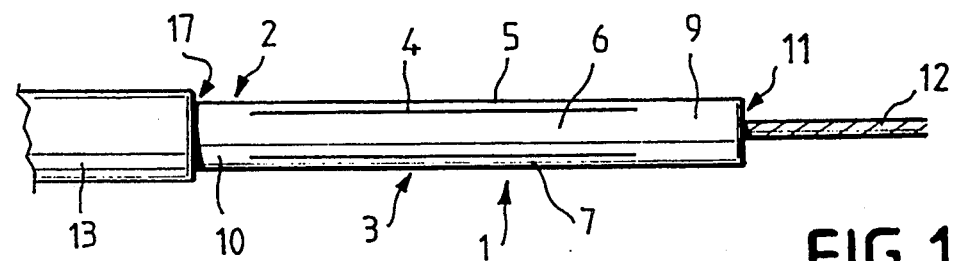
Figure 2:
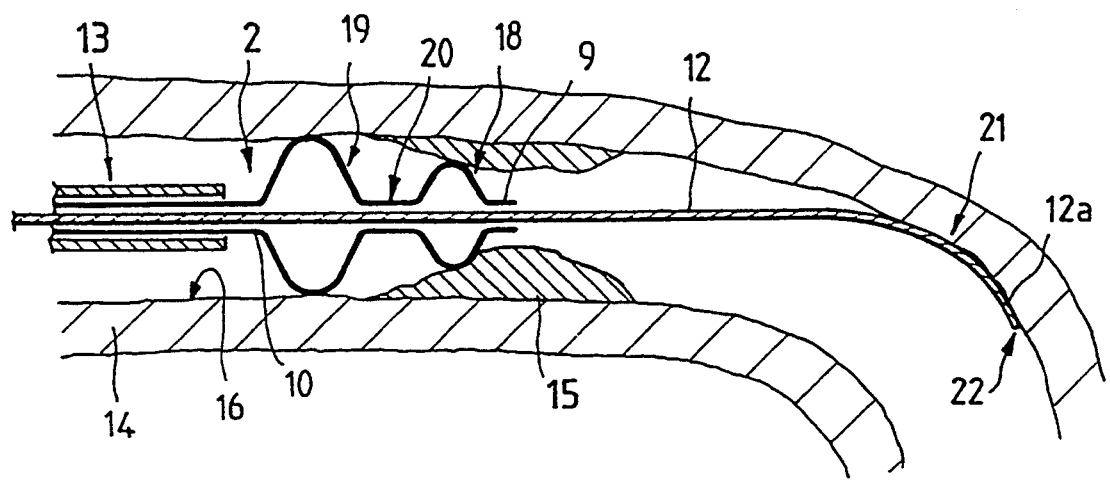
FIG. 2 is a cross-section of a device with two rotary tools placed inside a vessel.

The proximal end of the conduit 2, which is not visible on FIGS. 1 and 2, also comprises means for driving it in rotation. Such means are known per se, they may be mechanical drive means such as those described in document EP 0086048 or preferably, pneumatic drive means such as those described in document EP 0268228.

Said pneumatic means comprise a turbine equipped with blades, the rotation of which is obtained by tangential feeding of a compressed fluid. Said turbine is traversed through by an axial tube into which is force-fitted the proximal end of the conduit 2.

With such 8 turbine, it is possible to obtain very high speeds of rotation, of about 200,000 revs. per minute.

FIG. 1B shows the front part 3 of the conduit 2 in normal position, i.e. in the position where the conduit is not driven in rotation by the turbine or by any other driving means. The strips 5–8 are longitudinally rectilinear extending normally from the conduit 2 and the distal end 9.

When the conduit 2 is set in rotation and more particularly when the rotation reaches a certain speed, there occurs a progressive transversal expansion of the strips 5–8 under the effect of the centrifugal force caused by said rotation. Said transversal expansion causes the distal end 9 of the conduit 2 to move closer to the other proximal end 10 of the front part 3 of the conduit 2.

In the case of a conduit in polytetrafluoroethylene having a diameter comprised between 1.5 and 2 mm, each strip 5–8 having a length d comprised between 1 and 2 cm, a transversal expansion of the strip was obtained from a speed of rotation of about 30,000 revs/min. with a maximum transversal expansion being reached at 150,000 revs/min.

Two additional elements are necessary for using the device 1, i.e. on the one hand the guide wire 12 and on the other hand, the introduction catheter 13.

The guide wire 12 is a wire which must be altogether flexible in order to follow the often curving path of the vessel, and rigid in order to keep a hold on and guide the rotary atherectomy device according to the invention. Its distal end is generally made of a radiopaque material enabling easy locating of the position of the guide wire by fluoroscopy.

The catheter 13 is of a known type. Its inner diameter is sufficient to receive the conduit 2.

Positioning of the device I according to the invention is achieved by first introducing the guide wire 12 inside the vessel 14 beyond the part where the deposits 15 adhering to the inner wall 16 of the vessel 14 are situated. Then the catheter 13 containing the conduit 2 is introduced into the vessel, said conduit 2 being itself force-fitted over the guide wire 12. Once the front edge 17 of the catheter 13 is stopped by the deposits 15, said catheter 13 is withdrawn while the conduit 2 is locked in position in such a way as to release the front part 3 of the conduit 2. Finally, the conduit 2 is set in rotation so as to produce the transversal expansion of the strips 5-8 as described hereinabove. The conduit 2 is then moved forwardly until the strips 5-8 reach the deposits 15 and gradually abrade them. During this operation, the operator can move the conduit 2 forward and then backward from the front, so that the strips 5-8 eliminate the deposits 15. At the same time, the operator can also alter on the speed of rotation of the driving turbine in order to improve the efficiency of penetration of the rotary tool of the invention.

FIG. 2 illustrates an atherectomy device according to the invention, in operation, the device comprising two successive sets 18 and 19 of flexible filiform elements with centrifugal transversal expansion.

In the case of a conduit of the type of that described in the preceding example illustrated in FIG. 1, the two sets 18 and 19 are obtained by making in the conduit slits such as indicated hereinabove, in two definite zones separated by an intermediate part 20 of conduit. Said intermediate part 20 of conduit enables the strips of the first set 18 to remain joined together and to the distal end 9, and the strips of the second set 19 to remain joined together and to the proximal end 10.

When the turbine or the means driving the conduit 2 are set in rotation, the first and second sets of strips start to gradually expand transversely. The first set 18, which is closest to the distal end 9 of the conduit 2 is the first one to come into contact with the deposits 15. Once the first set 18 has sufficiently eroded the deposits 15, it is possible, by moving the conduit 2 forward, to actuate the second set 19 so as to eliminate any remaining deposits sticking to the inner wall 16 of the vessel 14.

As can be seen in FIG. 2, the guide wire 12 rests, at its fore part 12a against the inner wall 16 of the vessel 14 at the level of a bent portion 21. Thus, the guide wire 12 is wedged in position and no flapping can occur during the rotation of the conduit 2, which flapping would be detrimental as it could, on the one hand, cause a degradation of the inner wall 16 at the level of the front end 22 and of the guide wire 12, and on the other hand, disturb the action of the rotary tool or tools.

As regards the atherectomy device with two sets of transversely expandable strips, it would be possible first to actuate only the first set 18, the second set 19 being left inside the catheter 13, and then to actuate the second set 19 after the conduit 2 has been moved inside the catheter 13 so that said second set can come out of said catheter 13.

In the case where thrombi require to be fragmented, this can be done at high speed by one of the devices described hereinabove. On the contrary, to abrade hard deposits inside the arteries, the surface of the flexible filiform elements with centrifugal transversal expansion should be abrasive. It is then possible to obtain a progressive erosion of these hard deposits.

If the conduit is made in a plastic material, such as for example polytetrafluoroethylene, the abrasive surface can be obtained either by sticking an abrasive powder, such as for example diamond powder, on the surface of the front part 3 of the conduit, or by incorporating an abrasive powder in the plastic material, at the level of the front part 3, during molding of the conduit 2.

Preferably also, the front edge 11 of the conduit 2 should also have an abrasive surface, so that said front edge 11 acts first on the deposits 15, notably in the case of an important obstruction of the vessel.

The invention is not limited to the embodiments described hereinabove by way of example and non-restrictively. In particular, the number of flexible filiform elements constituting the rotary tool, can be more or less than four, being generally at least three and at most eight.

In the foregoing examples, the diameter of the rotary tool, when the filiform elements are rectilinear, was of 1.7 mm. This diameter can be even smaller since the only obligation is that of being able to introduce the guide wire into the corresponding conduit, knowing that the guide wire can be very fine. It is thus possible, with the device according to the invention, to act inside vessels of very small diameter, say for example 2 mm.

What is claimed is:

1. An atherectomy/thrombectomy device for clearing a blood vessel or the like, comprising a thin, elongated flexible tubular assembly having a rotatable inner member with a thin wall, a hollow distal end portion and a remote proximal end portion, means for connecting said proximal end portion to a high speed rotational drive means, an outer conduit containing said inner member and having a proximal end secured against the high speed rotation, said inner member having in said distal end portion a series of longitudinal slits extending through said thin wall and therearound to define a pattern of narrow parallel flexible filiform elements, said filiform elements being radially outwardly expandable upon rotation of said inner member at the high speed under the sole effect of centrifugal forces thereby causing said filiform elements to expand while rotating in said high speed.

2. The atherectomy or thrombectomy device of claim 1, wherein the outward expansion of the filiform element sis obtained from a speed of rotation of the rotary inner member higher than 30,000 revs./min.

3. The atherectomy or thrombectomy device of claim 1, including a guide wire which is rigid and designed to be threaded through the hollow inner member and extends to the distal end thereof over a length sufficient to locate said distal end at a predetermined location within said blood vessel.

4. The atherectomy or thrombectomy device of claim 1, wherein the conduit is made of polytetrafluoroethylene.

5. The atherectomy or thrombectomy device of claim 1, wherein the flexible filiform elements of the rotary member have an abrasive surface.

6. The atherectomy or thrombectomy device of claim 5, wherein the abrasive surface is obtained by mixing an abrasive powder with the plastic material constituting the rotary inner member, at least in its distal end portion corresponding to the rotary filiform elements.

7. The atherectomy or thrombectomy device of claim 1, wherein the rotary member is composed of two successive sets of flexible filiform elements situated respectively toward the distal end and the proximal end.

8. The atherectomy or thrombectomy device of claim 7, wherein the length of the filiform elements of the distal end set is smaller than the length of the filiform elements of the proximal end set.

* * * * *